US011452495B2

United States Patent
Pourtaherian et al.

(10) Patent No.: US 11,452,495 B2
(45) Date of Patent: Sep. 27, 2022

(54) APPARATUS AND METHOD FOR DETECTING A TOOL

(71) Applicant: KONINKLIJKE PHILIPS N.V., Eindhoven (NL)

(72) Inventors: Arash Pourtaherian, Eindhoven (NL); Hendrikus Hubertus Maria Korsten, Eindhoven (NL); Nenad Mihajlovic, Eindhoven (NL); Jinfeng Huang, Eindhoven (NL); Peter Hendrik Nelis De With, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 749 days.

(21) Appl. No.: 15/779,562

(22) PCT Filed: Dec. 5, 2016

(86) PCT No.: PCT/EP2016/079691
§ 371 (c)(1),
(2) Date: May 29, 2018

(87) PCT Pub. No.: WO2017/097682
PCT Pub. Date: Jun. 15, 2017

(65) Prior Publication Data
US 2020/0297303 A1   Sep. 24, 2020

(30) Foreign Application Priority Data
Dec. 7, 2015   (EP) .................................... 15198142

(51) Int. Cl.
*A61B 8/00*   (2006.01)
*A61B 8/08*   (2006.01)
(Continued)

(52) U.S. Cl.
CPC ............ *A61B 8/0841* (2013.01); *A61B 8/483* (2013.01); *A61B 8/523* (2013.01); *A61B 8/5207* (2013.01);
(Continued)

(58) Field of Classification Search
CPC .... A61B 2034/2063; A61B 2034/2065; A61B 2090/378; A61B 34/20; A61B 8/0841; A61B 8/483; A61B 8/5207; A61B 8/523
See application file for complete search history.

(56) References Cited

U.S. PATENT DOCUMENTS 5,817,022 A    10/1998  Vesely
2012/0321154 A1  12/2012  Korsten et al.
(Continued)

FOREIGN PATENT DOCUMENTS

JP   2012139437 A   7/2012
JP   2013099386 A   5/2013

OTHER PUBLICATIONS

Mari et al "Ultrasonic Scanning of Strait Micro Tools in Soft Biological Tissues" Ultrasonics, vol. 51, No. 5, Jan. 11, 2011 p. 632-638.
(Continued)

*Primary Examiner* — Mark D Remaly

(57) ABSTRACT

The apparatus is adapted to detect a tool based on a 3D image obtained by a 3D ultrasound imaging system. The apparatus comprises an image processing unit, which includes a tool detection module configured to perform a tool detection procedure. The tool detection procedure involves identifying a shadow of the tool in the 3D image and calculating the position of a "tool plane section" of the 3D image in which the entire length of the tool is represented.

10 Claims, 7 Drawing Sheets

(51) Int. Cl.
*A61B 34/20* (2016.01)
*A61B 90/00* (2016.01)

(52) U.S. Cl.
CPC ...... *A61B 34/20* (2016.02); *A61B 2034/2063* (2016.02); *A61B 2034/2065* (2016.02); *A61B 2090/378* (2016.02)

(56) References Cited

U.S. PATENT DOCUMENTS

| | | |
|---|---|---|
| 2013/0218024 A1 | 8/2013 | Boctor et al. |
| 2013/0229504 A1 | 9/2013 | Cheng |
| 2014/0058268 A1 | 2/2014 | Mitchell |
| 2014/0121505 A1 | 5/2014 | Irisawa |
| 2014/0187947 A1 | 7/2014 | Hansegaard et al. |
| 2014/0228678 A1* | 8/2014 | Meyer .................. A61B 6/487 600/424 |
| 2015/0002538 A1 | 1/2015 | Sohn et al. |

OTHER PUBLICATIONS

A. Pourtaherian, S. Zinger, P. H. N. de With, H. H. M. Korsten, and N. Mihajlovic, "Gabor-Based Tool Detection and Tracking in Three-Dimensional Ultrasound Data Volumes," in Proc. IEEE Int. Conf. Image Processing (ICIP), 2014, pp. 3602-3606.

Ding et al "Automatic Needle Segmentation in Three-Dimensional Ultrasound Images Using Two Orthogonal Two-Dimensional Image Projections" Medical Physics, vol. 30, No. 2, Feb. 1, 2003, p. 222-234.

* cited by examiner

US 11,452,495 B2

APPARATUS AND METHOD FOR DETECTING A TOOL

This application is the U.S. National Phase application under 35 U.S.C. § 371 of International Application No. PCT/EP2016/079691 filed on Dec. 5, 2016, which claims the benefit of EP Application Serial No. 15198142.0, filed Dec. 7, 2015. These applications are hereby incorporated by reference herein.

FIELD OF THE INVENTION

The present invention relates to an apparatus and method for detecting a tool, and in particular to an apparatus and method for imaging an interventional tool using images obtained by ultrasound imaging.

BACKGROUND OF THE INVENTION

Ultrasound imaging is one of the most popular imaging systems for tool guidance applications. Ultrasound imaging may be used to image tools such as needles, laparoscopes, stents, and radioactive seeds used for brachytherapy. For example, ultrasound imaging may be used for needle guidance in anesthesiology, tissue ablation or for biopsy guidance, since needles are used to take tissue samples, and to deliver medicine or electrical energy to the targeted tissue inside a patient's body. During these procedures, visualization of the needle and its tip is very important in order to minimize risk to the patient and improve health outcomes.

Typically, 2D ultrasound guidance is used to visualize a tool while a procedure is being conducted. However, this mode of imaging has a number of drawbacks. In particular, 2D imaging has a limited field of view; after a successful alignment and localization of the tool in the ultrasound image and while moving the tool or assessing the target, any undesired hand motion of the person conducting the procedure may cause misalignment of the tool and the ultrasound transducer such that parts of the tool are excluded from the ultrasound image. This may lead to incorrect placement of the tool. Furthermore, during the procedure, the focus of the operator may be diverted from treatment, as they may be distracted by searching for the tool in the ultrasound image.

External tool tracking systems also have a number of disadvantages, since they require additional equipment, which adds to the cost of the ultrasound imaging system. Further, a specialized needle comprising additional sensors is required. Limiting the physician to the use of a specialized needle will likely add to the cost of the procedure.

3D ultrasound imaging may be used as an alternative to a 2D ultrasound system. 3D ultrasound systems have a large field of view and therefore the tool can be easily captured, improving needle guidance. To provide guidance with a 3D ultrasound system, appropriate image-based analysis is necessary in order to detect and visualize the tool. Detection of the long-axis plane of the tool is particularly important. By detecting the long-axis plane, it is possible to locate the tool and to visualize planes including the tool to the user. Performance of image-based tool detection is limited; inherent issues with ultrasound imaging include low signal-to-noise ratio, speckle noise and anisotropy in images. Therefore, detecting a tool with ultrasound imaging in realistic clinical situations is difficult.

Recently, tool detection techniques have been proposed in 3D ultrasound based on directionally sensitive spectral transformations, which are shown to be more robust to noise and can detect the needle in challenging situations.

Nevertheless, these proposals do not enable detection of a tool when the insertion angle of the tool (the angle between the incident ultrasound radiation and the tool) is large. In these cases, incident beams are reflected at large angles and, as a consequence, are not detected by the ultrasound imaging system. Accordingly, the tool is almost invisible in the acquired data set.

FIGS. 1A and 1B show a typical ultrasound imaging system and illustrate the insertion angle of a tool 1, together with a corresponding ultrasound image of the tool 1. An ultrasound apparatus 3, comprising an ultrasound emitter and an image sensor, is arranged to emit ultrasound waves 5 towards a subject. They form incident ultrasound radiation to the subject. The ultrasound apparatus 3 acquires a dataset which, based on the reflected ultrasound radiation, is used to image the tool 1. The emitted ultrasound radiation propagates in a direction substantially perpendicular to the emission surface 7 of the ultrasound apparatus 3.

The tool 1 is inserted at an angle to the emission surface 7 of the ultrasound apparatus 3. The insertion angle of the tool is the angle between the emission surface 7 of the ultrasound apparatus 3 and the tool 1, wherein the emission surface of the ultrasound apparatus 3 is a plane perpendicular to the transmission direction of the incident ultrasound radiation 5.

In FIG. 1A, the tool is shown at a small insertion angle; the tool is arranged substantially parallel to the emission surface 7 of the ultrasound apparatus 3. In this case, the insertion angle of the tool 1 is about 0°. The ultrasound radiation 5 is reflected by a surface of the tool 1, and propagates back towards the ultrasound apparatus 3, where it is detected by the image sensor. Since the tool strongly reflects the incident ultrasound radiation, it appears as a bright region in the ultrasound image.

In FIG. 1B, the tool 1 and ultrasound apparatus 3 are provided in a different arrangement, in which the insertion angle of the tool 1 is large. In this case, the angle between the emission surface 7 of the ultrasound apparatus 3 and the tool 1 is about 45°. The ultrasound radiation 5 propagates towards the tool 1 and is incident on a reflective surface of the tool 1. Some of the ultrasound radiation is reflected at a large angle, causing it to be directed away from the image sensor. Consequently, the tool 1 is almost invisible in the ultrasound image produced by the ultrasound apparatus 3.

There is therefore a need for an apparatus and method for detecting a tool with 3D ultrasound imaging even when the tool is inserted at a large angle with respect to the emission surface of the ultrasound apparatus.

SUMMARY OF THE INVENTION

The invention is defined by the claims.

According to examples, in accordance with an aspect of the invention, there is provided an apparatus for detecting a tool comprising:

an image processing unit adapted to detect a tool based on a 3D ultrasound image, comprising:

a first tool detection module configured to perform a first tool detection procedure comprising:

obtaining a set of planar sections from the 3D ultrasound image;

identifying a tool shadow region present in a planar section of the set of planar sections; and determining the location of a tool plane section within the 3D image, wherein the tool plane section represents a plane within the 3D image in which the entire length of the tool is present, based on the detected tool shadow region.

In 3D ultrasound imaging, a 3D ultrasound imaging apparatus is arranged to emit ultrasound radiation towards a subject and to detect radiation reflected by the subject to produce a 3D volume data set which represents a 3D volume of the subject. In this way, the 3D imaging apparatus produces an image of the 3D volume.

The image processing unit is adapted to process the 3D image obtained by the 3D ultrasound imaging apparatus to determine which plane of the 3D image represents a plane of the 3D volume that includes the entire length of the tool, including a tip of the tool. This plane is called the tool plane section. By performing the first tool detection procedure, the tool plane section is rapidly identified enabling the position and orientation of the tool to be efficiently and reliably determined. By detecting the position of the tool plane section, it is possible to visualize the long-axis view of the tool. In addition, other views of the tool can be determined with respect to the tool plane section. For example, a plane including a short-axis of the tool can be identified since it is a plane perpendicular to the tool plane section. Further, since the image processing unit processes a typical 3D ultrasound image to determine the position of the tool plane section, the apparatus can be incorporated into a typical 3D ultrasound imaging system without requiring modification of any of the other elements of the system.

The first tool detection module locates the tool plane section based on a region of the 3D data set that represents a shadow of the tool. In this way, the location of the tool can be detected even when the insertion angle of the tool is large since a shadow of the tool is identifiable regardless of the insertion angle.

The first tool detection module is configured to obtain a set of planar sections from the 3D ultrasound image which represent sections of the 3D volume that are perpendicular to the transmission direction of the ultrasound radiation incident on the 3D volume. The first tool detection module may select a sub-set of these planar sections of the 3D image by selecting planar sections that are located beneath the tool, on an opposite side of the tool to ultrasound radiation incident on the tool.

After the planar sections have been selected, the first tool detection module is configured to detect dark regions in at least one of the planar sections and to identify a tool shadow region from the detected dark regions. The tool shadow region is a dark region that corresponds to a shadow of the tool.

The first tool detection module may analyze the detected dark regions to determine whether the dark region is likely to represent a shadow of the tool, for example by examining the size, width and/or shape of the dark region and comparing it to an expected size, width and/or shape of the shadow of the tool.

The first tool detection module calculates the position of a planar section of the 3D volume data set that includes the entire length of the tool or a portion of the tool that is present in the imaged 3D volume, based on the position of the tool shadow region. This section of the 3D volume data is the "tool plane section".

The first tool detection module may be configured to identify a plurality of tool shadow regions by detecting dark regions present in a plurality of planar sections and determining whether the dark regions correspond to a shadow of the tool. In particular, if a dark region does correspond to a tool shadow, there will be corresponding dark sections in other planar sections. In this way, the risk of falsely identifying the tool from one planar section is avoided. Once the tool shadow has been identified, one planar section is sufficient to identify its orientation.

The first tool detection module may process the planar sections to detect whether the planar sections comprise any dark regions. The detected dark regions may include dark regions that do not relate to the tool shadow. The relative position of detected dark regions in different planar sections may then be analyzed to further narrow the set of dark regions to a subset which form the overall tool shadow. Therefore, the first tool detection module may determine whether the dark regions correspond to a tool shadow based on the relative position of other detected dark regions. The set of dark regions that are most consistent with each other may be identified as tool shadow regions, which form an overall tool shadow.

The first tool detection module may be configured to determine the orientation of the tool plane section based on the plurality of tool shadow regions, or the tool shadow in just one of the planar sections. The first tool detection unit may determine whether a plane is the tool plane section by determining the orientation at which dark regions in the planar sections are most consistent, for example using RANSAC (random sample consensus).

The apparatus may further comprise a second tool detection module which is configured to perform a second tool detection procedure comprising:

detecting the tool based on a representation of the tool in the 3D image, preferably using an intensity and/or frequency based algorithm.

At a shallow insertion angle, the tool is highly visible in the 3D image and therefore the tool can be directly identified from the 3D image. The tool strongly reflects incident ultrasound radiation towards the image sensor and therefore the position of tool is represented in the 3D image as a bright region, which can be detected using an appropriate algorithm. By providing the function of tool detection at shallow angles as well as steep angles, the apparatus can be used to detect tools over a range of insertion angles and is therefore suitable for many different applications.

The second tool detection procedure is suitable for identifying the position of the tool when the angle between the tool and the face of an ultrasound emitter of the 3D ultrasound imaging apparatus is a small angle, so that the tool can be directly identified from the 3D image. The range of insertion angles over which the tool is visible enough to detect directly will depend on the exact arrangement of the 3D imaging apparatus. However, in a typical arrangement the tool is unlikely to be visible at an insertion angle greater than 30°.

The 3D image is a 3D volume data set and comprises a plurality of volume elements. The second tool detection module may be configured to perform the second tool detection procedure by:

performing a Gabor transformation on the 3D volume data set;

implementing a feature vector for each volume element of the 3D volume data set; and classifying the plurality of volume elements of the 3D data set to extract a plurality of candidate tool volume elements.

In this way, regions of the 3D dataset that are likely to correspond to the needle are identified. By using directionally sensitive spectral transformations, the detection method is less sensitive to noise and can therefore detect the tool in more challenging situations. The second tool detection procedure may further comprise identifying candidate tool volume elements that do not correspond to the tool and discarding these elements. The second tool detection module may be configured to perform classification on only a sub-set of the volume elements. For example, to speed up processing the tool detection module may be configured to perform classification on every other volume element.

The apparatus may further comprise:
a controller configured to:
control the image processing unit to determine whether the tool is visible in the 3D image;
control the first tool detection unit to perform the first tool detection procedure, if the tool is not visible; and
control the second tool detection unit to perform the second tool detection procedure if the tool is visible.

The first and second tool detection modules may be configured to determine whether the tool is at a small insertion angle orientation or a large insertion angle orientation. The controller is configured to initiate the first tool detection procedure and/or the second tool detection procedure based on the detected orientation of the tool. In this way, the tool detection module is configured to automatically select the appropriate tool detection procedure for the insertion angle of the tool. This allows the tool plane section can be quickly identified, enabling rapid location of the tool plane section and visualization of the tool to the user. At small insertion angles both tool detection procedures may be used for increased accuracy.

The apparatus may further comprise:
an ultrasound emitter arranged to direct ultrasound radiation towards a 3D volume, and
an image sensor adapted to detect ultrasound radiation reflected by the 3D volume and generate a 3D image based on the detected ultrasound radiation, and wherein the image sensor is configured to communicate the 3D image to the image processing unit.

Therefore, the apparatus may provide an ultrasound guidance system for imaging a 3D volume in which at least a part of a tool is submerged. The ultrasound emitter directs ultrasound waves towards the 3D volume to be imaged and the image sensor detects ultrasound waves reflected by the 3D volume and produces an image of the 3D volume using the acquired data set. These images are then transmitted to the image processing unit which processes them to rapidly locate a planar section of the image in which the entire length of the tool is shown (the tool plane section).

The apparatus may further comprise a display unit for displaying an ultrasound image, wherein the image processing unit is configured to communicate an image of the tool plane section to the display unit. Once the location of the tool plane section in the 3D image is identified by the image processing unit, it sends an image of the tool plane section to the display unit. In this way, the tool plane section can be visualized and used for guidance.

According to an aspect of the invention, there is provided a method for detecting a tool using ultrasonic radiation, comprising:
obtaining a 3D volume data set; and
performing a first tool detection procedure, comprising:
obtaining a set of planar sections of the 3D volume data set, wherein each planar section represents a plane perpendicular to a transmission direction of the ultrasonic radiation;
identifying a tool shadow region in a planar section; and
determining the location of a tool plane section within the 3D volume data set, wherein the tool plane section represents a plane in which the entire length of the tool is present, based on the detected tool shadow region.

By performing this method, a plane of the 3D image that includes the entire length of the tool can be quickly identified, enabling rapid visualization of the tool to an operator. Also, the method is less sensitive to noise and therefore provides a reliable way to detect the location of the tool in a variety of situations. Further, the method can be used to detect the tool in high noise environments.

The method is concerned with processing an ultrasound image and is performed without requiring any input from a medical professional.

A plurality of tool shadow regions may be identified and the location of the tool plane section may be calculated based on the tool shadow regions.

Identifying a plurality of tool shadow regions may comprise detecting dark regions present in the planar sections and determining whether the dark regions correspond to a shadow of the tool. The tool shadow regions may be identified by finding a set of dark regions that are consistent with each other. The tool plane section may be detected by identifying a plane orientation for which the dark regions are most consistently aligned with that plane.

The position of the tool plane section may be determined by determining the orientation of the dark regions in one or more of the planar sections.

The method may further comprise, before performing the first tool detection procedure, determining whether the tool is visible in the 3D image, and if the tool is not visible, performing the first tool detection procedure.

The invention also provides a computer program comprising code means adapted to perform the method defined above when said program is run on a computer.

By providing a computer program the functionality of an existing image processing unit can be altered to detect a tool and locate a tool plane section, without altering any of the typical existing equipment used for 3D ultrasound imaging.

DETAILED DESCRIPTION OF THE EMBODIMENTS

The invention provides an apparatus for detecting a tool in which a 3D ultrasound image is processed by obtaining a set of planar sections from the 3D ultrasound image. A tool shadow region present in a planar section is identified, and the location of a tool plane section within the 3D ultrasound image is determined. The tool plane section represents a plane within the 3D image in which the entire length of the tool is present, based on the detected tool shadow regions. This then enables the tool to be visualized in the most effective way for the user of the system.

Figure 2:
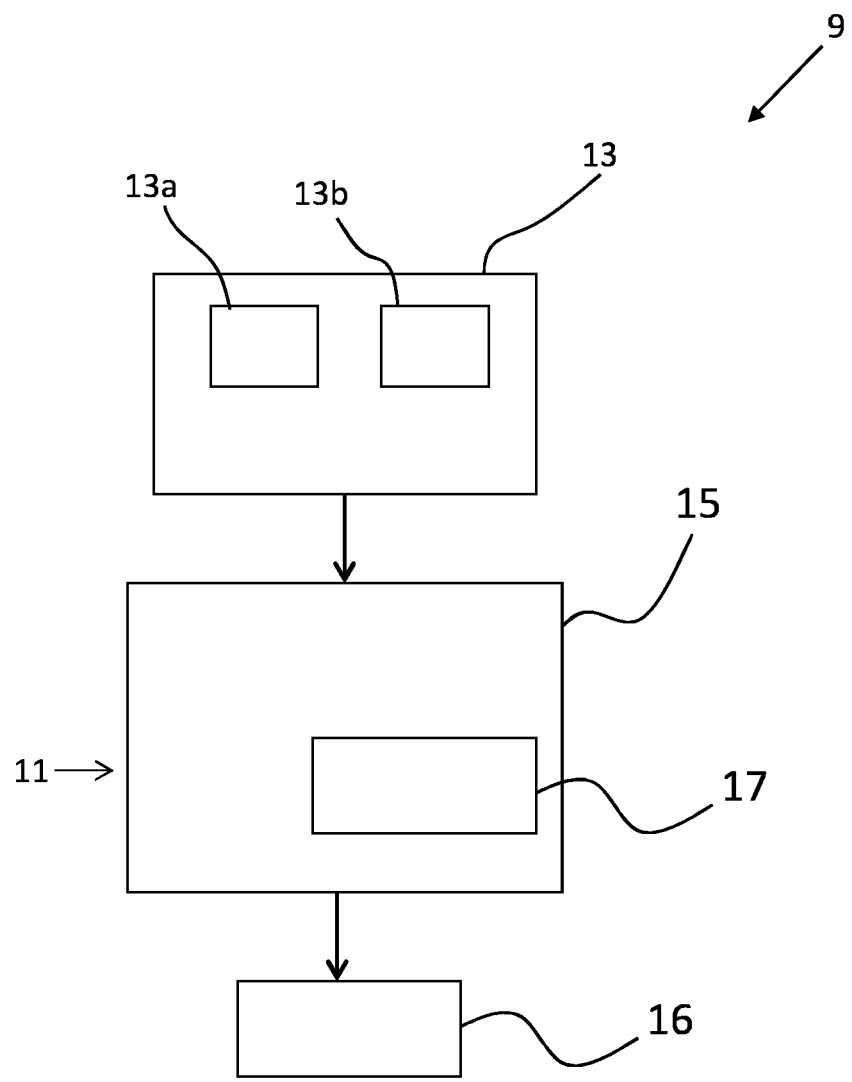
FIG. 2 is a schematic drawing of an ultrasound guidance system including an apparatus for detecting a tool according to an example.

FIG. 2 is a schematic block diagram illustrating an ultrasound guidance system 9 including an apparatus 11 according to an example. The apparatus 11 is adapted to detect a tool within a 3D image obtained by a 3D ultrasound imaging system 13 comprising an ultrasound emitter 13a and an image sensor 13b. The 3D ultrasound system may comprise an ultrasound probe (not shown). The ultrasound emitter 13a and the image sensor 13b may be located within the ultrasound probe as a part of an ultrasound array. The probe may also comprise integrated circuitry arranged to control the array during the ultrasound beam emission (transmission) and reception. The probe may partially (or fully) process the signals corresponding to ultrasound radiation reflected by the 3D volume, which may be further communicated to a main unit (not shown) of the ultrasound system 13. The main unit of the ultrasound system is arranged to generate a 3D ultrasound image of the volume based on the partially (of fully) processed signals, said 3D image is then communicated to an image processing unit 15.

The apparatus 11 comprises the image processing unit 15, which includes a tool detection module 17 configured to perform a tool detection procedure. The tool detection procedure involves identifying a shadow of the tool in the 3D image and calculating the position of a "tool plane section" of the 3D image in which the entire length of the tool is represented. The tool detection procedure enables rapid location of the tool plane section. In this way, the image processing unit is capable of efficiently detecting the tool section plane, whilst being robust to noise. By obtaining this information, rapid and accurate visualization of the tool is enabled on a display 16.

In FIG. 2 the apparatus is an image processor. In this case, the apparatus 11 can be incorporated into an ultrasound guidance system 9 without requiring modification of other components of the ultrasound imaging equipment.

The apparatus 11 is configured to communicate with a 3D ultrasound imaging system 13. The apparatus is configured to receive a 3D image from the 3D ultrasound imaging system and to process the 3D image using the image processing unit 15. The 3D ultrasound imaging system is, for example, suitable for imaging an interventional tool such as a needle.

Figures 1A, 1B:
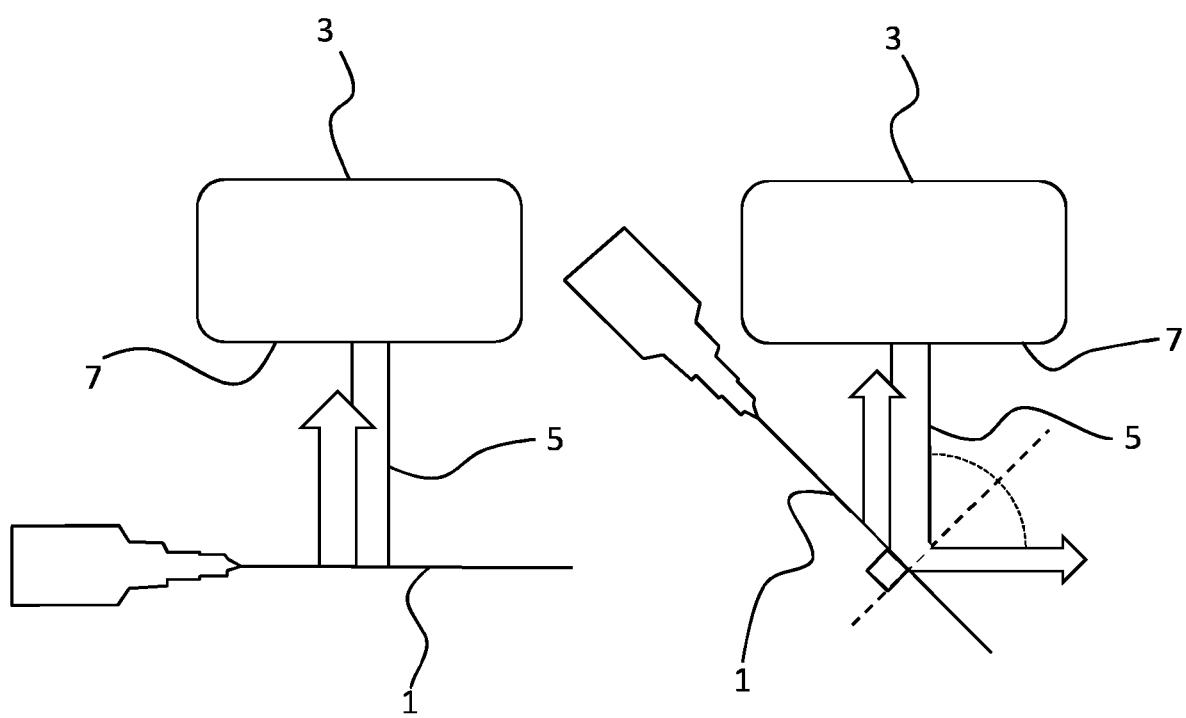
FIG. 1A shows an ultrasound imaging apparatus with a tool disposed at a small insertion angle of an interventional tool.
FIG. 1B shows an ultrasound imaging apparatus with a tool disposed at a large insertion angle of an interventional tool.

A further advantage of the apparatus is that it can be used to detect a tool over a large range of insertion angles. In a typical ultrasound guidance procedure, the tool is located by detecting a bright region of the 3D image which represents the tool. However, since the 3D volume is imaged by detecting reflected radiation, the tool is difficult to detect in situations where the insertion angle of the tool is large. This is because the ultrasound radiation is reflected by the tool at a large angle, and therefore is not detected by the image sensor (as illustrated by FIG. 1B). Therefore, at large insertion angles, visibility of the tool in the 3D image is poor.

The image processing unit detects the tool section plane by detecting a shadow of the tool in the 3D image. This enables the tool to be detected, even when the tool is orientated in such a way that visibility of the tool is poor, for example between 45 degrees and 90 degrees. The visibility of a needle decreases significantly with increasing the insertion angle. Therefore, for insertion angles larger than 30°, detection of a normal needle (not special or echogenic) is very likely to fail or to be unreliable.

An outer surface of the tool strongly reflects incident ultrasound radiation and therefore most of the ultrasound radiation incident on the tool is reflected, irrespective of the orientation of the tool. Some of the incident radiation is transmitted, but the intensity is of the transmitted beams is significantly lower than that of the reflected beams. Therefore, a region of the image that represents a side of the tool opposite to the side on which ultrasound radiation is incident is relatively dark. This effect is particularly strong when the insertion angle of the tool is large since a larger proportion of the incident ultrasound beams are reflected away from the image sensor. Accordingly, the shadow of the tool can be detected over a wide range of insertion angles.

Figure 3:
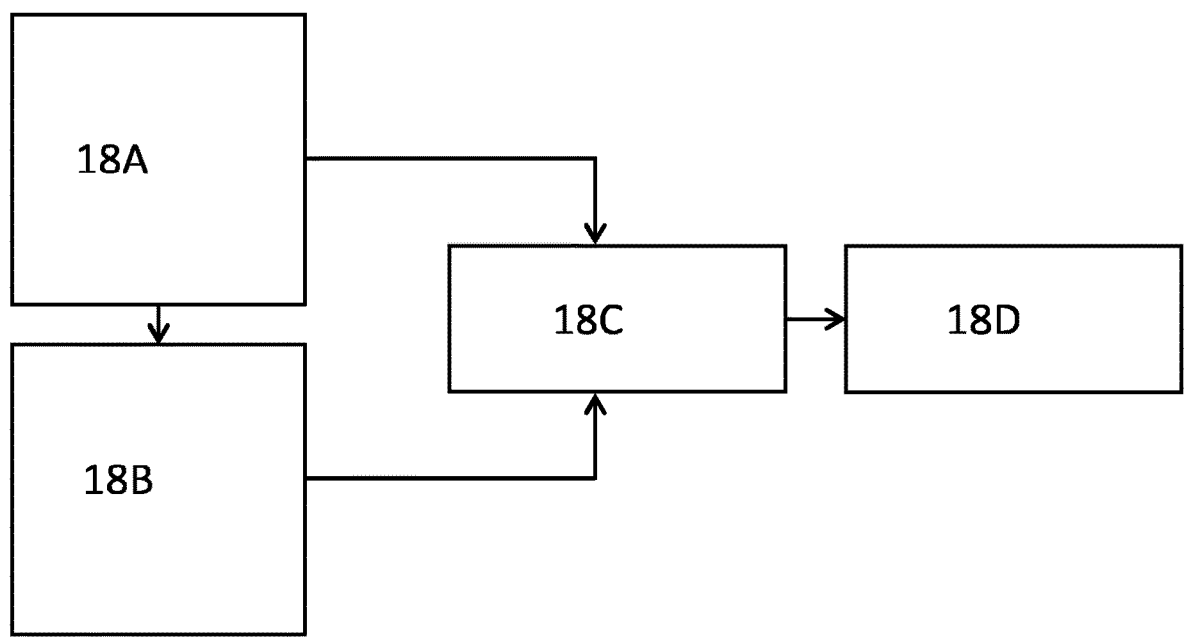
FIG. 3 illustrates a method for detecting a tool according to an example.

FIG. 3 illustrates the tool detection procedure performed by the image processing unit according to an example of the invention.

In a first step (18A) of the tool detection procedure, a set of planar sections is obtained from a 3D ultrasound image, generated by the 3D ultrasound imaging system. The planar sections represent sections of the imaged 3D volume located below the tool, which are perpendicular to the transmission direction of ultrasound radiation emitted by the ultrasound imaging system. The shadow of the tool is most visible in these planar sections of the 3D image. Therefore, using these planar sections to locate the tool enables fast and accurate identification of the tool shadow. The planar sections are obtained at different depths of the 3D image, providing a set of planar sections.

Next, in step 18B, the planar sections obtained in step 18A are analyzed to detect dark regions of the planar sections that may represent a shadow of the tool. In sections beneath the needle, a shadow of the needle will appear as an ellipsoidal blob, which is relatively dark to a neighboring region of the 3D image. Therefore, after de-noising the image and performing analysis techniques such as negative thresholding, line detection or segmentation techniques, dark regions having the properties typical of the tool shadow can be identified. Further enhancement can be implemented by examining the size, width and shape of the dark regions, since the size, width and shape of the needle is known and therefore an expected size, width and shape of the shadow can be calculated. However, not all the dark regions present in the planar sections correspond to a shadow of the tool. Therefore, some of the detected dark regions do not form part of the tool shadow.

Next, in step 18C, the dark regions detected in step 18B are processed to identify which of the dark regions correspond to the tool shadow. By identifying at least one tool shadow region, it is possible to determine the location of a plane of the 3D image which represents the full length of the needle along a longitudinal axis of the volume.

The location of the tool section plane may be determined based on the position of a single detected tool shadow region, or multiple tool shadow regions from different planar sections which together form a detected overall shadow.

There are different ways to process the planar sections to identify the dark regions which are tool shadows. These tool shadow regions are a subset of the detected dark regions. To identify this subset, a random sample and consensus algorithm (RANSAC) is performed on the data set. In the RANSAC method, a fitting model is determined and elements of the dataset are checked to determine which elements are consistent with the fitting model. The tool shadow region subset is a subset of the dataset that has minimal outliers.

In one example, in order to locate the tool shadow region subset, a possible tool plane is chosen, and the number of detected dark regions in sections perpendicular to the tool plane section that are consistent with the possible tool plane section are counted. Alternatively, or additionally, the number of sections perpendicular to the transmission direction of ultrasound radiation emitted by the ultrasound imaging system that include dark regions consistent with the possible tool plane are counted.

This process is repeated for several iterations until the possible tool plane with the maximum number of inliers is identified; this is the actual tool plane. The dark regions that intersect with the tool plane section are tool shadow regions which form an overall tool shadow. Therefore, by identifying the plane that includes the overall tool shadow, the orientation of the tool plane section is determined based on the tool shadow regions.

In step 18D, a section of the volume parallel to the ultrasound beams and containing the full length of the detected overall shadow is calculated and visualized to the user. This section is the tool plane, which contains the full-length needle and the tip. Other views of the needle may also be located based on the position of the tool plane section.

Figure 4A:
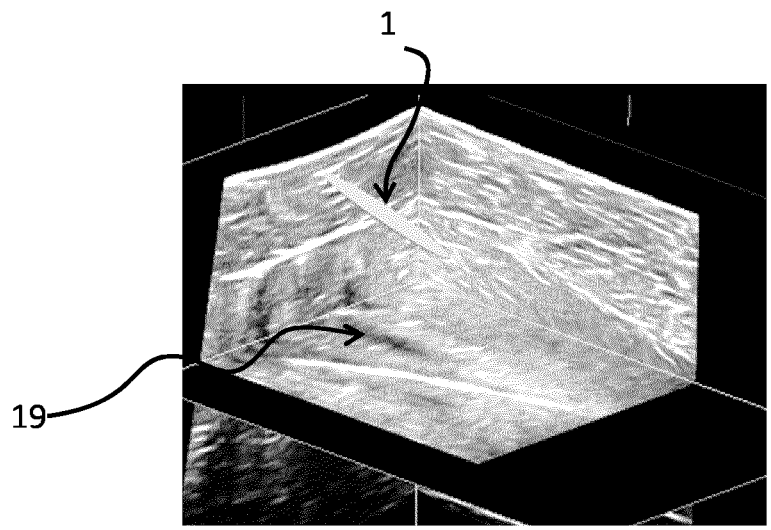
FIG. 4A shows a 3D image of a volume obtained by ultrasound imaging.

FIG. 4A shows an example of a 3D ultrasound image of a needle 1, including a shadow of the needle 19.

Figure 4B:
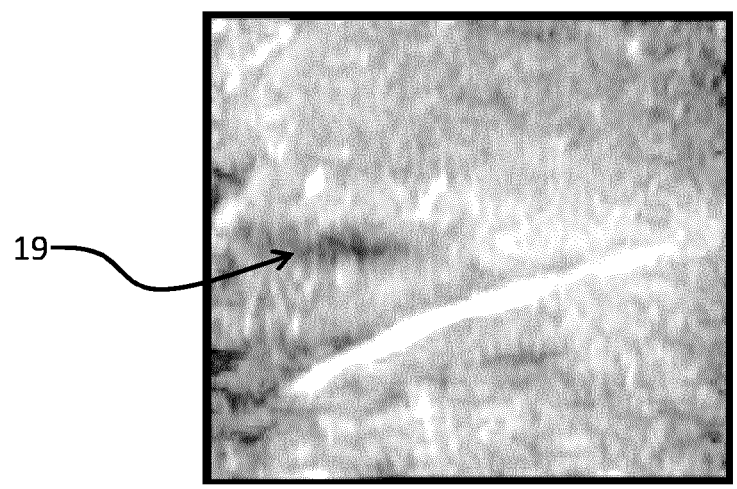
FIG. 4B shows a planar section of the volume of FIG. 4B.

FIG. 4B shows a planar section of the image of FIG. 4A, wherein the planar section is located underneath the needle. The planar section is obtained by the first tool detection module, and is subsequently subjected to noise reduction image processing. Dark regions are detected and analyzed to determine whether the dark region represents a shadow of the tool. Also, the planar section is perpendicular to the direction of incident ultrasound beams used to create the image, since planar sections of this orientation provide the most distinctive representation of the tool's shadow 19.

Figure 5:
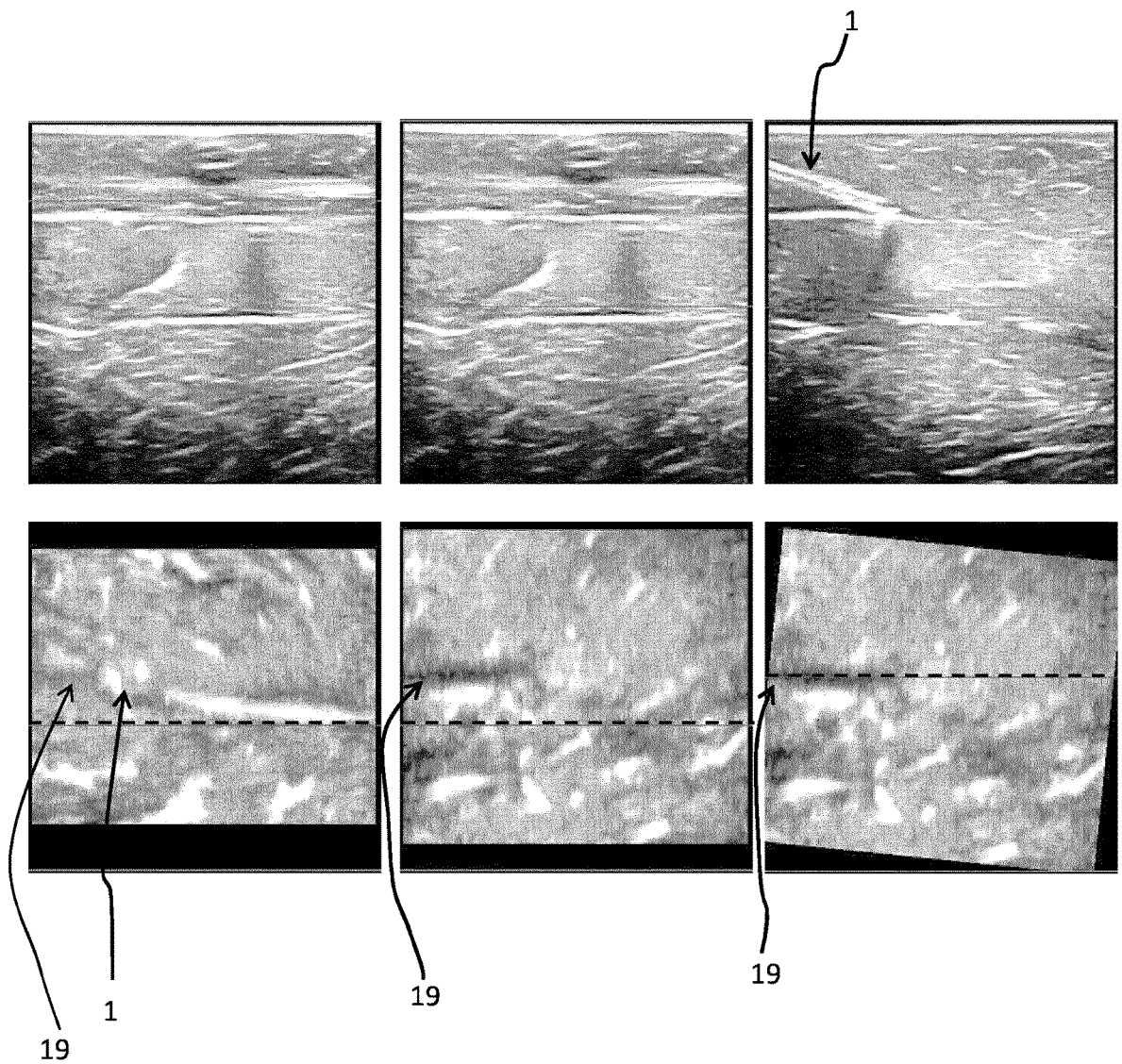
FIG. 5 shows a set of example planar images of a 3D volume, wherein a needle is disposed at a small insertion angle.

FIG. 5 shows an example of a planar section within a 3D image, wherein a needle 1 is disposed at small angle relative to the transmission direction of ultrasound radiation. The needle 1 has a relative angle of approximately 20° to the face of the transducer. In this case, shadowing is strong but the needle 1 is also still visible. Therefore, both intensity-based and shadowing-based detection techniques result in the correct long-axis needle plane. Therefore, either technique can be used to detect the needle.

The pair of images on the left hand side are cross sections of the 3D volume, wherein the top image is a cross section parallel to the direction of propagation of the ultrasound beam and the lower image is a cross section perpendicular to the direction of propagation of the ultrasound beam. The dotted line in the lower image show the cross sectional plane of the upper image. In the lower image, a small section of the needle 1 is visible as two bright circles. The circles represent the intersection of the plane with the lower wall and upper wall of the needle. A small part of the shadow 19 is also visible. Neither the needle nor the shadow of the needle is visible in the upper image, since the upper image is of a cross section of the 3D volume that does not intersect with the needle or the shadow of the needle (as shown by the separation between the dotted line and the needle/shadow in the lower image).

The central pair of images are cross sections of the 3D volume, wherein the lower image is a cross section perpendicular to the ultrasound beam located below the needle. The needle shadow is visible as region 19. The top image is again a cross section parallel to the ultrasound beam. The dotted line in the lower image again shows the cross sectional plane of the upper image. Thus, the upper image is again a cross section of the 3D volume that does not intersect with the needle; the cross section is located far from the needle. Note that the position of the dotted line is the same for both the left and central lower images. Thus, the left and central upper images are the same.

The pair of images on the right hand side show the detected needle section plane. The top image is a cross section parallel to the ultrasound beam and the lower image is a cross section perpendicular to the ultrasound beam.

The upper image cross section is rotated so that the needle lies fully in the plane. This can be seen from the lower image, in which the dotted line passes along the needle shadow 19. This is why the image is rotated clockwise compared to the other two images. In the top right image, the needle 1 is fully in the plane of the image. This is made possible by controlling the rotational angle of the vertical slice (i.e. the slice parallel to the propagation direction).

Thus, the "tool plane section" is a plane which includes both a vector parallel to the direction of propagation of the ultrasound radiation and a vector parallel to the elongate axis of the tool. The tool plane section intersects the tool. A plane can always be defined with which these two 2-dimensional vectors intersect. Thus, by controlling the position and rotation of the imaging plane—about an axis parallel to the direction of propagation—a "tool plane section" can be formed in which the general axial direction of the tool is located. A needle can clearly be represented by a two dimensional vector. However, the approach is also applicable to more three dimensional tools which have a general elongate axis. By locating this general elongate axis in the "tool plane section" the tool becomes as visible as possible.

Further, by locating the tool plane section, it is possible to locate other planes that include a section of the needle. Also, based on the location of the tool plane section, a non-planar section of the image that contains the whole tool can be constructed.

Figure 6:
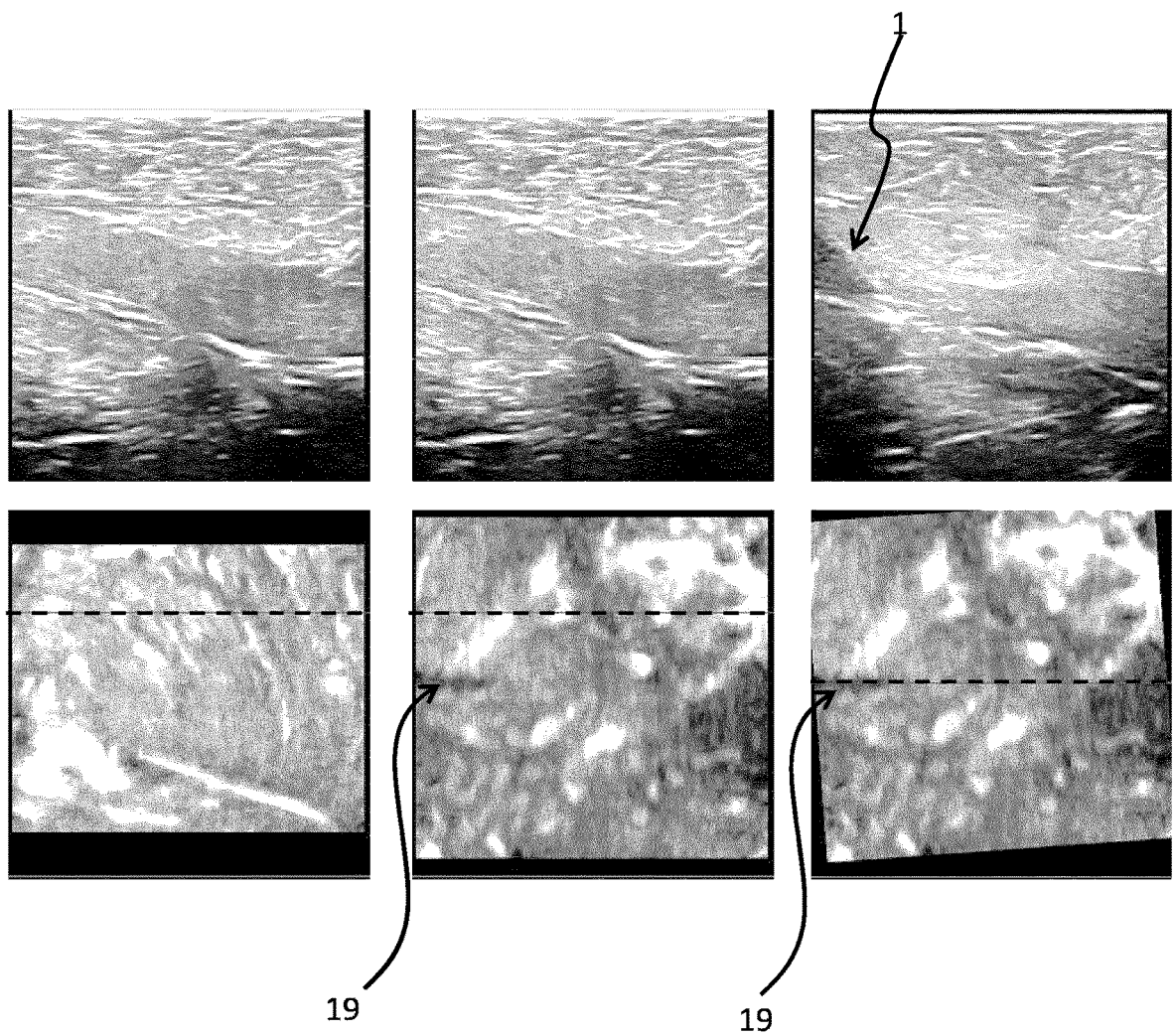
FIG. 6 shows a set of example planar images of a 3D volume, wherein a needle is disposed at a large insertion angle.

FIG. 6 shows an example planar image of a 3D volume, wherein a needle is disposed at a large angle relative to the transmission direction of ultrasound radiation; the needle is inserted with a steep angle of approximately 45°. As shown, despite the poor visibility of the needle, shadowing 19 is very strong and can be used to efficiently and accurately locate the tool plane section within the 3D image.

The pair of images on the left hand side are planar sections of the 3D volume. The top image is a cross section parallel to the direction of propagation of the ultrasound beam and the lower image is a cross section perpendicular to the direction of propagation of the ultrasound beam. The lower cross section is located above the needle, which cannot be seen in the image. Note that the bright white line at the bottom right of the left hand lower image represents soft tissue. In clinical ultrasound images of patients, other bright structures such as, bones, fatty structures, nerves and veins can be also present.

The central pair of images are cross sections of the 3D volume. The top image is a cross section parallel to the ultrasound beam and the lower image is a cross section perpendicular to the ultrasound beam. The shadow 19 can now be seen.

The pair of images on the right hand side show the detected needle section plane. The top image is a cross section parallel to the ultrasound beam and the lower image is a cross section perpendicular to the ultrasound beam.

As for the example of FIG. 5, the upper image cross section is positioned and rotated so that the needle lies fully in the plane. This can be seen from the lower image, in which the dotted line passes along the needle shadow 19.

In the top right image, the needle 1 now is visible and fully in the plane of the image. This is made possible by controlling the position and rotational angle of the vertical slice (i.e. the slice parallel to the propagation direction).

Figure 7:
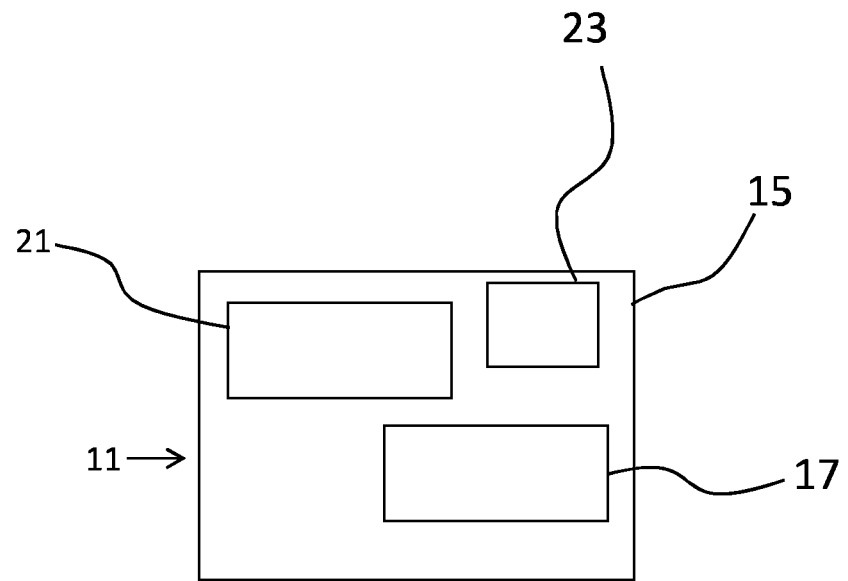
FIG. 7 is a schematic drawing of an apparatus for detecting a tool according to an example.

FIG. 7 shows an example of the apparatus for detecting a tool within a 3D ultrasound image. The apparatus 11 is an image processor. In this example, the image processing unit 15 comprises a second tool detection module 21, which operates in conjunction with the first tool detection module 17 to efficiently and robustly detect the long-axis needle plane in the 3D ultrasound volume.

The first tool detection module inspects the volume for dark regions of the 3D image that represent a shadow of the tool. This method is most beneficial in cases of large insertion angles but can also be used to detect a tool at small insertion angles. Therefore, shadow based tool detection is suitable for detecting a tool at any insertion angle.

The second module is adapted to detect the needle based on its 3D appearance when the needle is orientated at a small insertion angle. For example, the second module may be configured to detect the tool using an intensity and frequency based algorithm. Such an algorithm is discussed in H. H. M. Korsten, P. H. N. de With, and J. W. M. Bergmans, "Needle detection in medical image data," 2012, and A. Pourtaherian, S. Zinger, P. H. N. de With, H. H. M. Korsten, and N. Mihajlovic, "Gabor-Based Needle Detection and Tracking in Three-Dimensional Ultrasound Data Volumes," in Proc. IEEE Int. Conf. Image Processing (ICIP), 2014, pp. 3602-6, for example. As mentioned above, shadow based detection can be used to identify a needle for any insertion angle. By providing an apparatus 11 that is capable of tool detection by either method, the tool can be detected with increased robustness to noise and reliability of detection.

The apparatus 11 also includes a controller 23 which is configured to control the first and second tool detection modules to perform first and second tool detection procedures, respectively. The controller may be configured to control the image processing unit to determine whether the tool is visible from a 3D image. If the tool is visible, the controller may command the second tool detection unit to perform the second tool detection procedure. Alternatively, the controller may cause the first and second tool detection unit to perform tool detection, since shadow-based detection can be used for any tool insertion angle. If the image processing unit determines that the tool is not visible, the controller may cause the first tool detection unit to perform the second tool detection procedure.

In an example, the apparatus includes a display unit for displaying an ultrasound image. Once the image processing unit has determined the location of the tool plane section, it transmits the image to the display unit to visualize the tool plane section to a user.

The apparatus may be an image processor. Alternatively, in some examples, the apparatus comprises a 3D ultrasound imaging system for generating a 3D image and the image processing unit is configured to communicate with the 3D ultrasound imaging system to receive a 3D image generated by the 3D ultrasound imaging system and perform the first tool detection procedure on the received 3D image.

The apparatus may be suitable for use with any type of tool that can be imaged by ultrasound radiation. For example, a metal tool or a tool with a reflective coating. The tool may be a needle, a catheter, an electrode or a laparoscope, for example. The angular range over which visibility of the tool may depend on the type of tool.

The image processing unit may be configured to detect dark regions only for a subset of the planar sections obtained from the 3D ultrasound image.

The image processing unit may determine the location of the tool plane section based on a subset of tool shadow sections.

Figure 8:
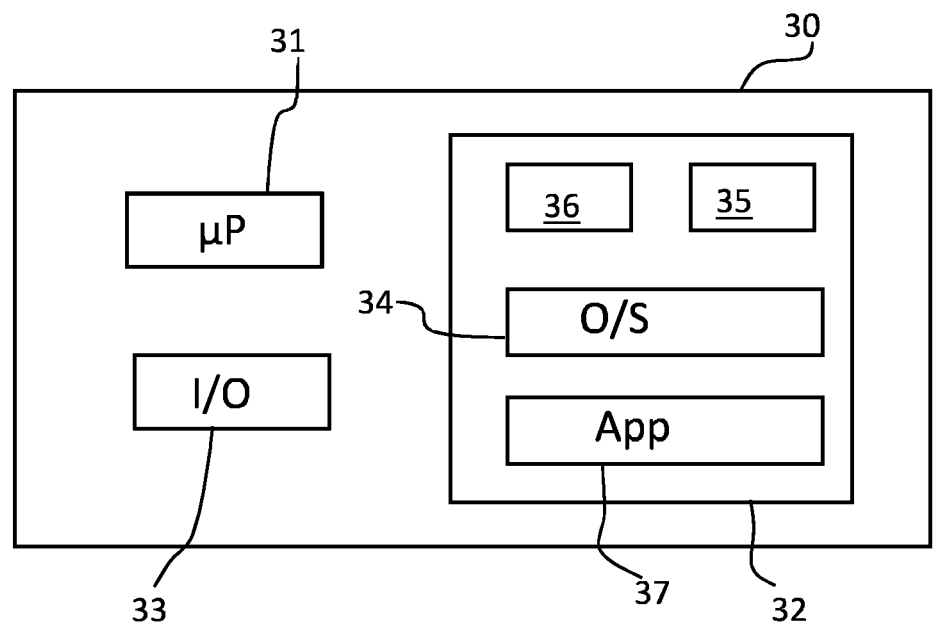
FIG. 8 shows a computer suitable for implementing the processing carried out by the apparatus.

As mentioned above, the image processing may be implemented by a controller. The controller may comprise a computer 30, as shown in FIG. 8.

The computer 30 includes, but is not limited to, PCs, workstations, laptops, PDAs, palm devices, servers, storages, and the like. Generally, in terms of hardware architecture, the computer 30 may include one or more processors 31, memory 32, and one or more I/O devices 33 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 31 is a hardware device for executing software that can be stored in the memory 32. The processor 31 can be virtually any custom made or commercially available processor, a central processing unit (CPU), a digital signal processor (DSP), or an auxiliary processor among several processors associated with the computer 30, and the processor 31 may be a semiconductor based microprocessor (in the form of a microchip) or a microprocessor.

The memory 32 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 32 may incorporate electronic, magnetic, optical, and/or other types of storage media. Note that the memory 32 can have a distributed architecture, where various components are situated remote from one another, but can be accessed by the processor 31.

The software in the memory 32 may include one or more separate programs, each of which comprises an ordered listing of executable instructions for implementing logical functions. The software in the memory 32 includes a suitable operating system (O/S) 34, compiler 35, source code 36, and one or more applications 37 in accordance with exemplary embodiments.

The application 37 comprises numerous functional components such as computational units, logic, functional units, processes, operations, virtual entities, and/or modules.

The operating system 34 controls the execution of computer programs, and provides scheduling, input-output control, file and data management, memory management, and communication control and related services.

Application 37 may be a source program, executable program (object code), script, or any other entity comprising a set of instructions to be performed. When a source program, then the program is usually translated via a compiler (such as the compiler 350), assembler, interpreter, or the like, which may or may not be included within the memory 320, so as to operate properly in connection with the operating system 340. Furthermore, the application 37 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 33 may include input devices such as, for example but not limited to, a mouse, keyboard, scanner, microphone, camera, etc. Furthermore, the I/O devices 33 may also include output devices, for example but not limited to a printer, display, etc. Finally, the I/O devices 33 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 33 also include components for communicating over various networks, such as the Internet or intranet.

When the computer 30 is in operation, the processor 31 is configured to execute software stored within the memory 320, to communicate data to and from the memory 320, and to generally control operations of the computer 30 pursuant to the software. The application 37 and the operating system 34 are read, in whole or in part, by the processor 310, perhaps buffered within the processor 310, and then executed.

When the application 37 is implemented in software it should be noted that the application 37 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Other variations to the disclosed examples can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An apparatus for detecting a tool comprising:
an image processing unit comprising a computer adapted to detect a tool based on a 3D ultrasound image, wherein the image processing unit is configured to:
determine whether the tool is visible in the 3D image;
when the tool is determined to not visible in the 3D image, perform a first tool detection procedure comprising:
obtaining a set of planar sections from the 3D ultrasound image;
identifying a tool shadow region present in a planar section of the set of planar sections; and
determining the location of a tool plane section within the 3D ultrasound image, wherein the tool plane section represents a plane within the 3D image in which the entire length of the tool is present, based on the detected tool shadow region;
when the tool is determined to be visible in the 3D image, perform a second tool detection procedure, the second tool detection procedure different from the first tool detection procedure, the second tool detection procedure comprising:
determining the tool based on a representation of the tool in the 3D image.

2. The apparatus of claim 1 wherein the for the first tool detection procedure, the image processing unit is configured to identify a plurality of tool shadow regions by detecting dark regions present in a plurality of planar sections and determining whether the dark regions correspond to a shadow of the tool.

3. The apparatus of claim 2 wherein the for the first tool detection procedure, the image processing unit is configured to determine the orientation of the tool plane section based on the plurality of tool shadow regions.

4. The apparatus of claim 1 wherein detecting the tool by the image processing unit based on the representation of the tool in the 3D image for the second tool detection procedure comprises using an algorithm based on intensity, frequency, or a combination thereof.

5. The apparatus of claim 4, wherein the 3D image is a 3D volume data set and comprises a plurality of volume elements, and the image processing unit is configured to perform the second tool detection procedure by:
performing a Gabor transformation of a 3D volume data set;
implementing a feature vector for each volume element of the 3D volume data set; and
classifying the plurality of volume elements of the 3D data set to extract a plurality of candidate tool volume elements.

6. An ultrasound system comprising:
an apparatus of claim 1;
an ultrasound emitter arranged to direct ultrasound radiation towards a 3D volume; and
an image sensor adapted to detect ultrasound radiation reflected by the 3D volume, wherein the ultrasound system is configured to generate a 3D image based on the detected ultrasound radiation and to communicate the 3D image to the image processing unit.

7. The ultrasound system of claim 6 further comprising a display unit for displaying an ultrasound image, wherein the image processing unit is configured to transmit an image of the tool plane section to the display unit.

8. A method for detecting a tool using ultrasonic radiation, comprising:
obtaining a 3D volume data set;
determining whether the tool is visible in a 3D image;
performing the first tool detection procedure responsive to the tool being not visible in the 3D image;
wherein performing the first tool detection procedure comprises:
obtaining a set of planar sections of the 3D volume data set, wherein each planar section represents a plane perpendicular to a transmission direction of the ultrasonic radiation;
identifying a tool shadow region in a planar section of the set of planar sections,
wherein a plurality of tool shadow regions are identified based at least in part on the identifying of the tool shadow region and the location of the tool plane section is calculated based on the tool shadow regions,
wherein the identifying the plurality of tool shadow regions comprises:

detecting dark regions present in the planar sections; and determining whether the dark regions correspond to a shadow of the tool, and wherein determining whether a dark region in one planar section corresponds to a shadow of the tool comprises determining whether the dark region is consistent with dark regions of other planar sections; and determining the location of a tool plane section within the 3D volume data set, wherein the tool plane section represents a plane in which the entire length of the tool is present, based on the detected tool shadow region.

9. The method of claim 8 further comprising:

performing a second tool detection procedure responsive to the tool being visible in the 3D image, the second tool detection procedure comprises:

determining the tool based on a representation of the tool in the 3D volume data set.

10. A computer program comprising code means adapted to perform the method of claim 8 when said program is run on a computer.

\* \* \* \* \*